United States Patent [19]

Micheli

[11] 4,279,666
[45] Jul. 21, 1981

[54] OXIDIZED ALUMINUM OVERCOAT FOR SOLID ELECTROLYTE SENSOR

[75] Inventor: Adolph L. Micheli, Mt. Clemens, Mich.

[73] Assignee: General Motors Corporation, Detroit, Mich.

[21] Appl. No.: 97,906

[22] Filed: Nov. 28, 1979

[51] Int. Cl.³ .................. C23C 11/00; B05D 5/12
[52] U.S. Cl. ............................ 148/6.3; 427/126.4;
427/383.3; 427/376.2; 427/376.3; 204/195 S;
428/329
[58] Field of Search ............ 427/383.1, 376.2, 376.7,
427/245, 255.4, 126.4, 383.3, 383.7, 376.3,
376.6; 204/195 S; 428/329; 148/6.3

[56] References Cited

U.S. PATENT DOCUMENTS

| | | | |
|---|---|---|---|
| 2,172,207 | 9/1939 | Kolligs et al. ........................ 427/78 |
| 3,182,376 | 5/1965 | Sprague et al. ..................... 29/25.41 |
| 3,314,124 | 4/1967 | Okamoto et al. .................... 29/25.41 |
| 3,632,498 | 1/1972 | Beer ................................. 204/290 F |
| 3,713,870 | 1/1973 | Kage ................................. 427/383.7 |
| 3,720,985 | 3/1973 | Buescher .......................... 427/383.7 |
| 3,998,375 | 12/1976 | Rudd ................................ 204/195 S |
| 4,021,326 | 5/1977 | Pollner et al. .................... 204/195 S |
| 4,097,353 | 1/1978 | Kishida et al. ...................... 427/243 |
| 4,116,883 | 9/1978 | Rhodes ................................ 252/463 |

OTHER PUBLICATIONS

Seiyama et al. "Study of a Detector for Gaseous Components Using Semiconductive Thin Films" *Analytical Chemistry*, V.33, n. 8, pp 1069–1073 (Jul. 1966).

*Primary Examiner*—Ronald H. Smith
*Assistant Examiner*—Richard Bueker
*Attorney, Agent, or Firm*—Robert J. Wallace

[57] ABSTRACT

An inexpensive method for making a durable porous overcoat on a noble metal exhaust electrode of a solid electrolyte exhaust gas oxygen sensor. The electrode is coated with aluminum flakes and the aluminum flakes oxidized in situ by heating in an oxidizing atmosphere.

3 Claims, No Drawings

OXIDIZED ALUMINUM OVERCOAT FOR SOLID ELECTROLYTE SENSOR

FIELD OF THE INVENTION

This invention relates to a solid electrolyte exhaust gas oxygen sensor. It more particularly relates to a method of forming a porous overcoat on the exhaust electrode of such sensors.

BACKGROUND OF THE INVENTION

U.S. Pat. No. 4,021,326 Pollner et al describes using a porous overcoat on the exhaust electrode of a zirconia-type exhaust gas oxygen sensor. Such a coating not only prevents erosion of thin film exhaust electrodes but also can provide a greater residence time of exhaust gases on the exhaust electrode surface. Obviously, the overcoat should be of an abrasion-resistant material and should be porous. The aforementioned Pollner et al patent describes forming the porous overcoat by calcining a coating of raw oxides in situ, or by sintering a coating of the desired oxide material to the zirconia. It can also be applied by flame spraying, or plasma spraying. The aforementioned Pollner et al patent also describes applying the overcoat by thin layer techniques such as thermal evaporation, precipitation from gases, and reactive vapor deposition. U.S. Pat. No. 4,116,883 Rhodes describes applying a water slurry of very fine alumina particles and then merely drying the coating at 500°–800° C. Flame spraying has been commercially used to overcoat zirconia-type sensors. On the other hand, such a technique is expensive. The coating technique described in the aforementioned Rhodes patent has also been commercially used. However, this latter type of coating is primarily useful for catalyst support purposes. If a catalyst is not used in the overcoat, this latter coating may not be preferred. Also, I do not expect that it is as durable as a sintered or flame sprayed coating.

I have found a new method of forming a porous overcoat on a noble metal exhaust gas electrode of a zirconia-type exhaust gas oxygen sensor. My coating is formed inexpensively and yet provides high porosity and durability.

OBJECTS AND SUMMARY OF THE INVENTION

It is therefore an object of this invention to provide a new method of making a porous covering on a noble metal exhaust electrode of a solid electrolyte exhaust gas oxygen sensor.

The invention comprehends coating a platinum exhaust electrode of a zirconia-type exhaust gas oxygen sensor with aluminum flakes. The aluminum flakes are then oxidized by heat treatment in an oxidizing atmosphere, to form an adherent porous matrix of aluminum oxide in situ.

Other objects, features and advantages of this invention will become more apparent from the following description of preferred embodiments thereof.

DESCRIPTION OF THE PREFERRED EMBODIMENTS

A zirconia solid electrolyte body such as described in U.S. Pat. No. 3,844,920 Burgett et al can be exteriorly overcoated in accordance with this invention. The zirconia body shown in U.S. Pat. No. 3,844,920 Burgett et al is a tapered thimble having a thick lip-flange. The exhaust gases contact the outer surface of the thimble below the flange. The entire outer surface of the thimble is coated with a porous thin film of platinum up to the flange. One technique for applying such a thin film is disclosed in United States patent application Ser. No. D-4,219, entitled "Exhaust Electrode Process for Exhaust Gas Oxygen Sensor", filed Oct. 29, 1979 in the names of T. J. Gold, F. L. Kennard, III, P. C. Kikuchi and R. V. Wilhelm, Jr. and assigned to the assignee of this invention. In accordance with this invention, the porous platinum thin film is overcoated with a 0.2 millimeter thick coating of flaked aluminum powder. To insure that the flaked aluminum powder stays in place during a subsequent heat treatment in accordance with this invention, I prefer to mix the aluminum powder with a temporary binder. To ease application of the powder-binder mixture, I prefer to thin it with an appropriate vehicle, and thus form a slurry. Such slurries are commercially available as high temperature aluminum paints. Paints such as these are available in ready-to-spray forms. One spray paint that can be used is HP4-14, available from Plasti-kote Co. of Medina, Ohio. This particular spray paint contains 13.4% by weight substantially pure aluminum flake and 5% by weight of an acrylic resin. The acrylic resin serves as the temporary binder.

An electroded zirconia thimble is overcoated in accordance with this invention by rotating the thimble on its axis while spraying a thin paint film onto it. The film can be dried with a heat gun, and the procedure repeated until the aforementioned coating thickness of about 0.2 mm is obtained. The coated thimble is then heated slowly to burn out the acrylic resin and oxidize the aluminum flakes.

A group of thimbles coated as described above was placed in a room temperature furnace and heated in air at a rate of about 70° C. per hour up to a temperature of about 600° C., and held there for about two hours. A second group of thimbles coated as described above was placed in a room temperature furnace and heated in air at about 70° C. per hour up to about 800° C., and held there for about one hour. The thimbles were then cooled, and some of each group assembled into exhaust gas oxygen sensors.

An adherent overcoat of aluminum oxide was formed in both heat treatments. The overcoat was porous and adherent in both heat treatments, and the resultant sensors performed generally similarly. Tests showed that the organic binder started to burn out from the overcoating at about 200° C., and finished burning out at about 450° C. Aluminum oxidation then accelerated and at about 600° C. a significant portion of the aluminum in the flakes appeared to be oxidized. By the time the aforementioned second group of thimbles were heated to 800° C. for an hour, most of the aluminum in the flakes was oxidized. Coating thickness shrinks about 10–20% during the heat treatments. Accordingly, the resultant aluminum oxide coating was about 0.16–0.18 mm in thickness. Further, it is recognized that pure aluminum melts at about 660° C. However, a significant aluminum oxide structure apparently formed on the surface of the aluminum flakes before they reached a melting point temperature. Thus, the residual aluminum in the flakes apparently did not coalesce and reduce porosity of the film. On the other hand, residual aluminum in the flakes may have made them adhere better to one another, and for this reason complete oxidation may not be desired. Also this coating may have improved adhesion because of an aluminum reaction with the underlying platinum, to form lower melting alloy compositions that cement the oxide to the underlying platinum surface. In any event, scanning electron micrographs of the resultant electrode overcoatings from both of the aforementioned groups of thimbles show that the aluminum flakes produce a strong interlocking porous matrix of aluminum oxide.

Sensors produced by the aforementioned technique required a break-in period of 1–100 hours before sensor electrical characteristics stabilized. It is expected that the platinum electrode required the break-in period, not the overcoat in this invention. In any event, after the break-in period, the sensors performed within acceptable limits over extended durability testing.

It should be recognized that rather ordinary furnaces can be used to practice this invention. No special atmospheres, power supplies, or sophisticated equipment is needed to apply the aluminum flakes or oxidize them. Hence, the process of this invention is relatively inexpensive.

Also, although this invention was tested only on zirconia-type solid electrolyte thimbles, it is expected that it would also be useful with other solid electrolyte materials such as thoria. Analogously, I have described overcoating a platinum electrode. It is believed that this invention can be used to provide overcoats on other noble metals such as palladium, rhodium, gold, and the like.

It appears necessary that the aluminum particles be aluminum flake if a satisfactory overcoat is to be obtained. Tests show spheroidal-type aluminum particles do not make durable coatings. By aluminum flake I mean spheroidal aluminum particles which have been coined into flatness such as by milling or the like. Such particles will have highly irregular edges and major surfaces which are generally of a dimension about 10–100 times the flake thickness. A particle size of approximately 1–10 micrometer in major surface cimension is believed to be satisfactory, especially if used with flake thicknesses of about 0.01–1 micrometer. Tests in this invention employed flakes which were of substantially pure aluminum. However, it is expected that alloys of aluminum could also be used, provided that they did not provide oxides which would interfere with oxygen sensing on the electrode surface. In general, I would expect that aluminum alloys containing more than about 80% aluminum would be satisfactory. I intend to include such alloys by the word aluminum, as used in the claims hereof.

The aluminum flakes were described as being applied by spraying on a slurry. Neither the constituent proportions in this slurry nor its method of application is particularly critical. For convenience I prefer to apply the aluminum flakes by spraying. However, it could also be applied as a more viscous slurry by brushing, wiping, rolling, etc. For spraying, a convenient slurry would contain approximately 5–20% aluminum flakes and 5–15% by weight of a suitable organic binder with the balance being a volatile vehicle such as alcohol, acetone, hydrocarbon solvents, or the like. However, for brushing a somewhat lesser vehicle proportion may be desired. In most instances, I prefer a slurry in which the aluminum flake-to-binder ratio is approximately 2–3 parts aluminum flakes to 1 part binder.

I prefer to use a sufficiently thick coating of the slurry to produce a satisfactory aluminum oxide thickness, usually about 0.1–0.2 millimeter. Thicknesses of about 0.2 millimeter provide an additional protection against electrode erosion and contamination. This additional thickness can be readily accommodated by the sensor and in this invention does not significantly increase cost. Aluminum thicknesses greater than about 0.2 millimeter are believed to be unnecessary and may even slow down sensor switching time response. I consider aluminum oxide thicknesses greater than about 0.3 millimeter undesirable.

Although the aluminum flakes were oxidized in air in the aforementioned examples of this invention, it is believed that any oxidizing atmosphere could be used, and in some instances may even be preferred. In this latter connection it may develop that it may be desirable to use an oxygen supplemented air atmosphere to reduce the time required to initially oxidize the aluminum flakes so that they retain their irregular interlocked structure. For example, I have described heating the zirconia thimbles at a rate of 70° C. per hour from room temperature to 600° C. or to 800° C. and then holding at those temperatures for two hours or one hour. respectively. It is believed that above about 450° C., the aluminum flake is progressively oxidized so as to form an aluminum oxide exoskeleton on each aluminum flake. This exoskeleton interlocks with the exoskeleton on the next adjacent aluminum flake to form a porous aluminum oxide network. The network retains the flake-like character of the aluminum flakes from which it is derived. Since no binder is present, it is porous. Because of the hardness of the aluminum oxide and the interlocked flake-like nature of the coating it is durable.

Presumably any heating rate can be used to form the exoskeleton. It has been formed at 70° C. per hour and 100° C. per hour. So long as the heat treatment is kept below the melting point temperature of the aluminum flake, the rate of heating should not be critical. However, if a binder is used in the aluminum flake coating, one may wish to heat more slowly while burning out the binder. Otherwise, a non-uniform aluminum oxide coating can result, with large holes in it. If the maximum temperature of the heat treatment is to go above the aluminum flake melting point temperature, it should not do so before a sufficient exoskeleton is formed on the aluminum flakes to prevent coalescence of molten aluminum. After the binder is substantially gone, rapid heating to 500°–600° C. may be used, and a more oxidizing atmosphere than air may be desired, to accelerate formation of the exoskeleton. Also, it may not be necessary that the heat treatment completely oxidize each flake. It may only be necessary to form a significant, i.e. rigid or self-supporting, aluminum oxide coating on each flake. Hence, a dwell of less than two hours in air at 600° C. or one hour in air at 800° C., or the equivalent thereof, may not be preferred in some instances.

It is to be recognized that the sensors I made in accordance with this invention required a moderately long engine break-in period. However, the break-in period which was experienced in my tests may have been attributable to electrode processing, rather than the heat treatment in accordance with this invention. Accordingly, improved electrode processing may reduce and even eliminate break-in requirements. Still further, break-in may not be required if the sensor is given the nitrogen aging treatment described and claimed in U.S. patent application Ser. No. 030,747, entitled "Aging Treatment for Exhaust Gas Oxygen Sensor", which was filed in the names of Morris Berg, Slater W. Hawes, Frederick L. Kennard, III and Paul C. Kikuchi on Apr. 17, 1979.

The embodiments of the invention in which an exclusive property or privilege is claimed are defined as follows:

1. In a method of making a porous refractory overcoat on a noble metal electrode of a solid electrolyte exhaust gas oxygen sensor, the improvement which comprises:

coating a slurry of aluminum flakes onto the noble metal electrode, drying the coating, and then oxidizing the aluminum flakes in situ by heating the coating in an oxidizing atmosphere wherein a strongly bonded and durable flake-like porous refractory overcoat is inexpensively formed on the noble metal electrode.

2. In a method of making a porous refractory overcoat on a noble metal electrode of a solid electrolyte exhaust gas oxygen sensor, the improvement which comprises:

coating a slurry of aluminum flakes having a maximum dimension of about 10 micrometers, an organic binder and a vehicle onto the noble metal electrode, drying the coating and then heating the coating in an oxidizing atmosphere to at least form a rigid exoskeleton of aluminum oxide on each flake, that is interlocked with aluminum oxide exoskeletons on adjacent flakes wherein a strongly bonded and durable porous refractory overcoat about 0.1–0.3 millimeter thick is inexpensively formed on the noble metal electrode.

3. In a method of making a porous refractory overcoat on a platinum exhaust electrode of a zirconia-type exhaust gas oxygen sensor, the improvement which comprises:

applying a coating about 0.1–0.3 millimeter thick on said platinum electrode of a slurry containing about 1 part organic binder for every 2–3 parts aluminum flakes of a maximum dimension of about 1–10 micrometer, drying the slurry coating, heating the dried coating in air to burn out the binder, and then heating it further in air to a temperature of about 600°–800° C. for about 1–3 hours, effective to form a strongly bonded matrix of aluminum oxide that serves as a protective refractory overcoat on said electrode.

* * * * *